United States Patent
Goshayeshgar

(10) Patent No.: US 9,028,488 B2
(45) Date of Patent: May 12, 2015

(54) RADIO FREQUENCY CATHETER TO TARGET LIGAMENTUM FLAVUM

(71) Applicant: Kyphon Sarl, Neuchatel (CH)

(72) Inventor: Mojan Goshayeshgar, Atherton, CA (US)

(73) Assignee: Kyphon Sarl, Neuchâtel (CH)

( * ) Notice: Subject to any disclaimer, the term of this patent is extended or adjusted under 35 U.S.C. 154(b) by 113 days.

(21) Appl. No.: 13/803,146

(22) Filed: Mar. 14, 2013

(65) Prior Publication Data

US 2014/0276728 A1  Sep. 18, 2014

(51) Int. Cl.
*A61N 1/00* (2006.01)
*A61B 18/14* (2006.01)

(52) U.S. Cl.
CPC ....................... *A61B 18/14* (2013.01)

(58) Field of Classification Search
CPC ........................................ A61B 18/14
USPC ...................................... 606/27–41
See application file for complete search history.

(56) References Cited

U.S. PATENT DOCUMENTS

| 6,780,183 | B2 | 8/2004 | Jimenez et al. |
| 7,371,232 | B2 | 5/2008 | Scheib |
| 7,959,631 | B2 | 6/2011 | Dicarlo |
| 2003/0236455 | A1 | 12/2003 | Swanson et al. |
| 2005/0096647 | A1 | 5/2005 | Steinke et al. |
| 2012/0022574 | A1 | 1/2012 | Mafi et al. |
| 2012/0029511 | A1 | 2/2012 | Smith et al. |
| 2012/0053611 | A1 | 3/2012 | Saab et al. |
| 2012/0130363 | A1 | 5/2012 | Kim et al. |
| 2014/0236144 | A1* | 8/2014 | Krueger et al. ................. 606/41 |

FOREIGN PATENT DOCUMENTS

WO  2012122157 A1  9/2012

OTHER PUBLICATIONS

International Search Report and Written Opinion for PCT/US2014/024053, the counterpart application mailed on Jul. 17, 2014.

* cited by examiner

*Primary Examiner* — Scott Getzow

(57) ABSTRACT

A device for performing a surgical procedure comprising an elongated shaft extending between a proximal end and a distal end and including an outer surface and an inner surface, the inner surface defining a passageway. A stylet is configured for moveable disposal within the passageway of the elongated shaft. The stylet includes a blunt distal tip configured for disposal outside the distal end of the elongated shaft and to prevent damage to adjacent tissue. An expandable member includes a proximal end and a distal end. The proximal end of the expandable member is disposed with the distal end of the elongated shaft and the distal end of the expandable member is connected to the distal end of the stylet. At least one electrode disposed with the expandable member.

19 Claims, 2 Drawing Sheets

US 9,028,488 B2

RADIO FREQUENCY CATHETER TO TARGET LIGAMENTUM FLAVUM

TECHNICAL FIELD

The present disclosure generally relates to medical devices for the treatment of nerve pain, and more particularly to a surgical system and method employing a radio frequency catheter to coagulate and shrink a ligamentum flavum and an inflatable bone tamp for nerve destruction.

BACKGROUND

Standard methods of cutting tissue may include using a scalpel, scissors, and radio frequency energy. Electrosurgical procedures and techniques using radio frequency energy are currently used since they generally reduce patient bleeding and trauma associated with cutting operations. Additionally, electrosurgical ablation procedures, where tissue surfaces and volume may be reshaped, cannot be duplicated through other treatment modalities.

Minimally invasive procedures in nerve and/or soft tissue such as the spine or the breast, however, are difficult to perform using standard scissors and scalpel. Furthermore, in a closed environment, radio frequency current dissipates into the surrounding tissue causing a decreased ability to achieve a current at the cutting electrode of sufficiently high density to initiate a cut. To overcome this problem, high power settings are often required to initiate the cut which often is painful and increases thermal damage to the tissue whether using a standard or a custom electrosurgical generator.

Another problem associated with cutting tissue is the control of bleeding. Radio frequency energy controls bleeding by coagulating small blood vessels. Another method of controlling bleeding is through the use of heat. For example, some commercially available scalpels use direct heat to control bleeding. However, while the bleeding is generally controlled, the cutting of tissue is often slower than with radio frequency energy and the knife edge readily dulls. Other commercially available scalpels use ultrasonic energy generally at 50 kHz to heat the tissue so as to coagulate severed blood vessels but cut slower than a standard electrosurgical electrode and are costly as a custom ultrasonic generator is required.

A further disadvantage of using radio frequency energy is the generation of smoke. The smoke is malodorous and can contain airborne viral particles that may be infectious. Furthermore, the smoke often obscures visualization of the procedure. When the smoke becomes too dense, the procedure is delayed until the smoke is released through one of the trocar ports and after enough carbon dioxide gas has reinsufflated the abdominal cavity. This unnecessarily prolongs the operative time.

Radiofrequency (RF) energy is used in a wide range of surgical procedures because it provides efficient tissue resection and coagulation and relatively easy access to the target tissues through a portal or cannula. Conventional monopolar high frequency electrosurgical devices typically operate by creating a voltage difference between the active electrode and the target tissue, causing an electrical arc to form across the physical gap between the electrode and tissue. At the point of contact of the electric arcs with tissue, rapid tissue heating occurs due to high current density between the electrode and tissue. This high current density causes cellular fluids to rapidly vaporize into steam, thereby producing a "cutting effect" along the pathway of localized tissue heating. Thus, the tissue is parted along the pathway of evaporated cellular fluid, inducing undesirable collateral tissue damage in regions surrounding the target tissue site. This collateral tissue damage often causes indiscriminate destruction of tissue, resulting in the loss of the proper function of the tissue. In addition, the device does not remove any tissue directly, but rather depends on destroying a zone of tissue and allowing the body to eventually remove the destroyed tissue.

Present electrosurgical techniques used for tissue ablation may suffer from an inability to provide the ability for fine dissection of soft tissue. The distal end of electrosurgical devices is wide and flat, creating a relatively wide area of volumetric tissue removal and making fine dissections along tissue planes more difficult to achieve because of the lack of precision provided by the current tip geometries.

In addition, identification of the plane is more difficult because the large ablated area and overall size of the device tip obscures the physician's view of the surgical field. The inability to provide for fine dissection of soft tissue is a significant disadvantage in using electrosurgical techniques for tissue ablation, particularly in arthroscopic, otolaryngological, and spinal procedures.

Traditional monopolar RF systems can provide fine dissection capabilities of soft tissue, but may also cause a high level of collateral thermal damage. Further, these devices may suffer from an inability to control the depth of necrosis in the tissue being treated. The high heat intensity generated by these systems causes burning and charring of the surrounding tissue, leading to increased pain and slower recovery of the remaining tissue. Further, the desire for an electrosurgical device to provide for fine dissection of soft tissue may compromise the ability to provide consistent ablative cutting without significant collateral damage while allowing for concomitant hemostasis and good coagulation of the remaining tissue.

Further, the health care practitioner may have difficulty positioning the tip of the device in the optimal location to get an optimal and consistent clinical result. This may also result in unwanted necrosis of adjacent tissue, which can lead to clinical adverse events including subsequent repair of the necrotic tissue.

Accordingly, there is a need for devices and methods to provide efficient severing or cutting of nerve and/or soft tissue that can be used during a minimally invasive procedure and/or during an open surgical procedure. Further, there is also a need for devices and methods that provide fine dissection capabilities of nerve and/or soft tissue. Devices and methods that do not cause a high level of collateral thermal damage and allow for the control of necrosis in the tissue being treated are also needed. Devices and methods that provide efficient, controlled and safe debulking of tissue would also be beneficial.

SUMMARY

In one embodiment, in accordance with the principle so the present disclosure, a device for performing a surgical procedure is provided. The device includes an elongated shaft extending between a proximal end and a distal end and includes an outer surface and an inner surface, the inner surface defining a passageway. A stylet is configured for moveable disposal within the passageway of the elongated shaft. The stylet includes a blunt distal tip configured for disposal outside the distal end of the elongated shaft and to prevent damage to adjacent tissue. An expandable member includes a proximal end and a distal end. The proximal end of the expandable member is disposed with the distal end of the elongated shaft and the distal end of the expandable member is connected to the distal end of the stylet. At least one electrode disposed with the expandable member.

In one embodiment, a device for ablating tissue includes a cannula extending between a proximal end and a distal end and includes an outer surface and an inner surface, the inner surface defining a passageway. A stylet configured for moveable disposal within the passageway of the elongated shaft. The stylet includes a blunt distal tip configured for disposal outside the distal end of the elongated shaft and to prevent damage to adjacent tissue. An expandable cage including a proximal end and a distal end. The proximal end of the expandable cage is disposed with the distal end of the elongated shaft and the distal end of the expandable cage is connected to the distal end of the stylet. At least one RF electrode disposed with the expandable cage.

In one embodiment, a method for ablating tissue at a surgical site is provided. The method includes providing a device comprising: a cannula extending between a proximal end and a distal end and includes an outer surface and an inner surface, the inner surface defining a passageway, a stylet configured for moveable disposal within the passageway of the elongated shaft and the stylet includes a blunt distal tip configured for disposal outside the distal end of the elongated shaft and to prevent damage to adjacent tissue, an expandable cage including a proximal end and a distal end, wherein the proximal end of the expandable cage is disposed with the distal end of the elongated shaft and the distal end of the expandable cage is connected to the distal end of the stylet, and at least one RF electrode disposed with the expandable cage; creating an access path to the surgical site inserting the expandable cage into the surgical site and extending the stylet to expand the expandable cage and emitting RF signals through the electrodes to thermally ablate tissue.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
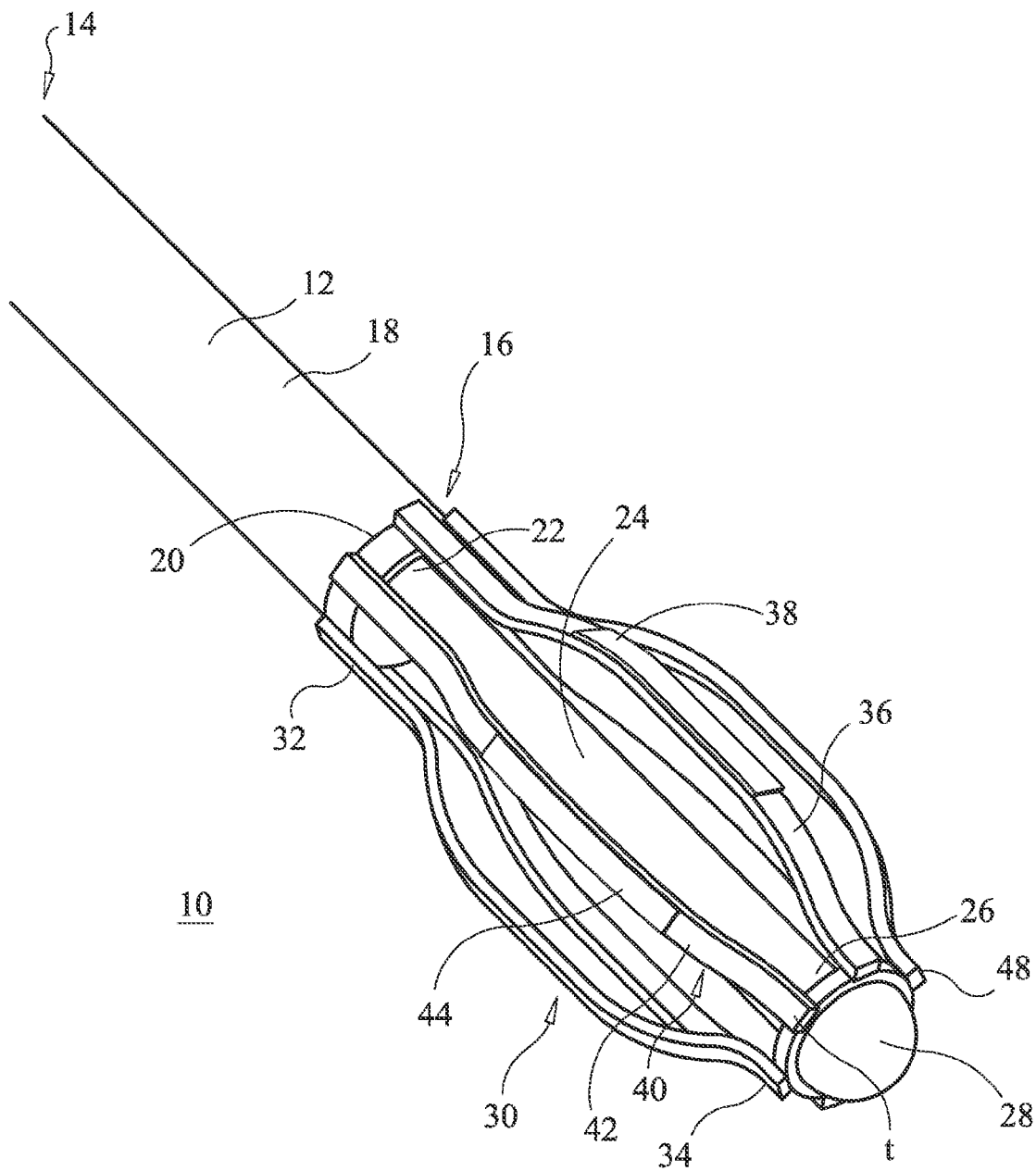
FIG. 1 is a perspective view, with partial cross section, of one embodiment of a surgical system in accordance with the principles of the present disclosure.

The exemplary embodiments of the surgical system and related methods of use disclosed are discussed in terms of medical devices for the treatment of musculoskeletal disorders and more particularly, in terms of a surgical system and method for nerve destruction.

Devices for efficient severing or cutting of a material or substance such as nerve and/or soft tissue suitable for use in open surgical and/or minimally invasive procedures are disclosed. The following description is presented to enable any person skilled in the art to make and use the present disclosure. Descriptions of specific embodiments and applications are provided only as examples and various modifications will be readily apparent to those skilled in the art.

Lumbar spinal stenosis (LSS) may occur from hypertrophied bone or ligamentum flavum, or from a lax ligamentum flavum that collapses into the spinal canal. LSS can present clinical symptoms such as leg pain and reduced function. Conventional treatments include epidural steroid injections, laminotomy, and laminectomy. Surgical interventions which remove at least some portion of the lamina are usually performed through a relatively large incision, and may result in spinal instability from removal of a large portion of the lamina. Consequently, a percutaneous approach which removes just enough tissue (lamina or ligamentum flavum) to be effective is provided.

In one embodiment, a deployable RF catheter is provided to target the hypertrophied ligamentum Flavum in Lumbar Spinal Stenosis. The system comprises an access cannula and a blunt stylet to access the ligamentum flavum through the interlaminar space. After access to the ligamentum flavum, the catheter will be deployed to the interlaminar space so as to distract the interlaminar space. The catheter placement will be confirmed under imaging guide. Then the catheter will be energized with RF at subablative controlled temperature. In one embodiment, the catheter may also include a balloon to distract the interlaminar space and deploy the basket.

The balloon can be constructed of one or multiple RF electrodes. The electrodes can be straight, helical or curved. The electrodes can be positioned inside, outside or within the wall of the balloon. The electrodes are deployed with the balloon. In one embodiment, a liquid pumping system may be connected to the balloon to inflate and cool down the inflation liquid dynamically (active cooling) or the balloon may be inflated with a cooled liquid (passive cooling).

It is contemplated that one or all of the components of the surgical system may be disposable, peel-pack, pre-packed sterile devices. One or all of the components of the surgical system may be reusable. The surgical system may be configured as a kit with multiple sized and configured components, such as, for example, inflatable members (balloons) that are preformed to have different sizes and shapes.

It is envisioned that the present disclosure may be employed to treat bones, and in particular arm bones such as a distal radius. It should be understood that the present principles are applicable to any bone structures, including but not limited to bones of the spine, legs, feet, arms, etc. It is contemplated that the present disclosure may be employed with other osteal and bone related applications, including those associated with diagnostics and therapeutics. It is further contemplated that the disclosed surgical system and methods may alternatively be employed in a surgical treatment with a patient in a prone or supine position, and/or employ various surgical approaches, including anterior, posterior, posterior mid-line, direct lateral, postero-lateral, antero-lateral, etc. approaches in the calcaneus, spine or other body regions. The present disclosure may also be alternatively employed with procedures for treating the muscles, ligaments, tendons or any other body part. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The components of system 10 can be fabricated from biologically acceptable materials suitable for medical applications, including metals, synthetic polymers, ceramics and bone material and/or their composites, depending on the particular application and/or preference of a medical practitioner. For example, the components of system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 10 may have material composites, including the above materials, to achieve various desired characteristics such as strength, rigidity, elasticity, compliance, biomechanical performance, durability and radiolucency or imaging preference.

The components of system 10, individually or collectively, may also be fabricated from a heterogeneous material such as a combination of two or more of the above-described materials. The components of system 10 may be monolithically formed, integrally connected or include fastening elements and/or instruments, as described herein.

Figure 2:
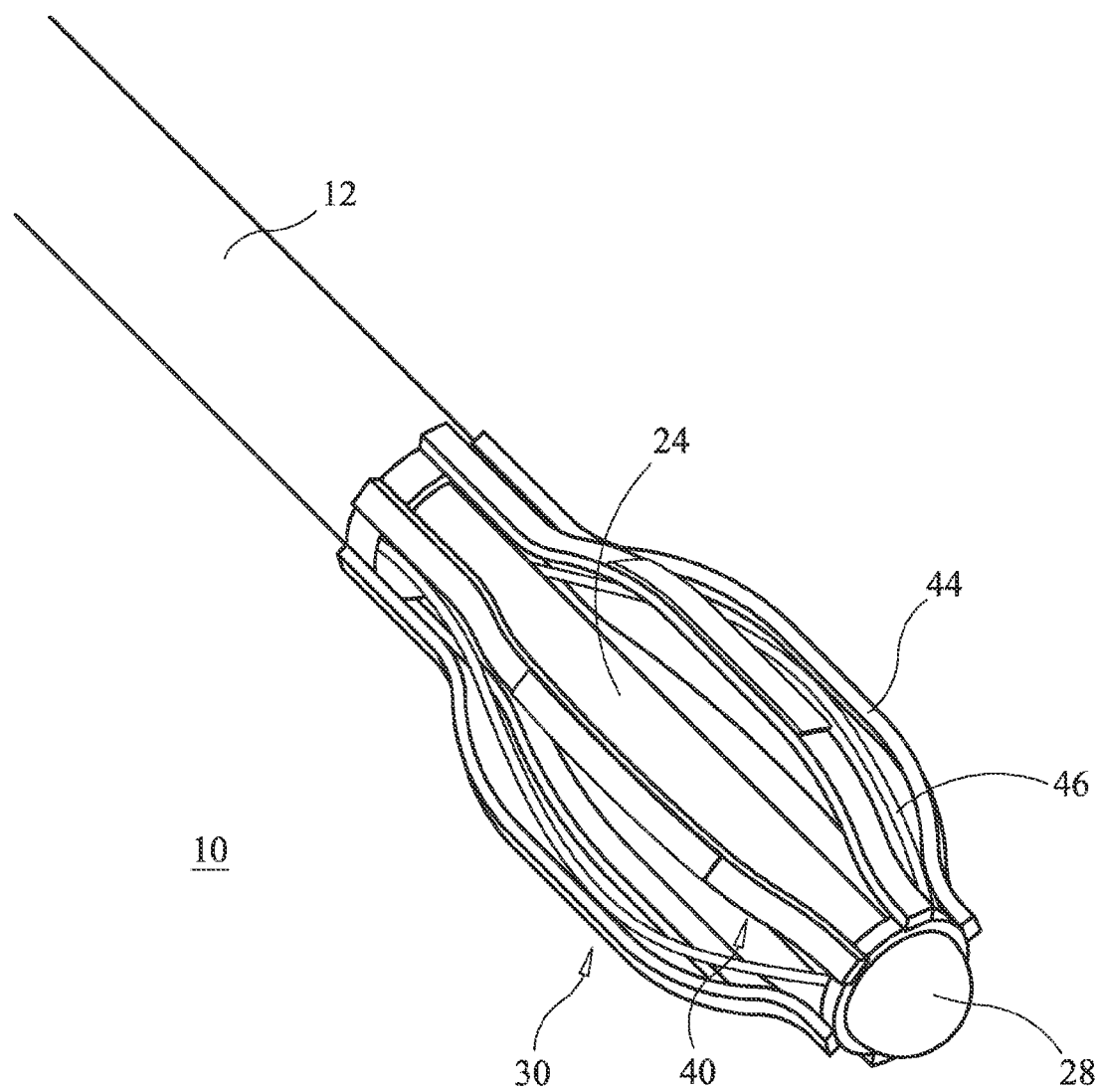
FIG. 2 is a perspective view, with partial cross section, of one embodiment of a surgical system in accordance with the principles of the present disclosure.

The following discussion includes a description of a system for performing a surgical procedure and related methods of employing the system in accordance with the principles of the present disclosure. Alternate embodiments are also disclosed. Reference will now be made in detail to the exemplary embodiments of the present disclosure, which are illustrated in the accompanying figures. Turning now to FIGS. 1-2, there are illustrated components of the system for performing a surgical procedure in accordance with the principles of the present disclosure.

As shown in FIGS. 1-2, balloon system 10 includes an elongated shaft, such as, for example, a cannula 12. Cannula 12 extends between a proximal end 14 and a distal end 16. Cannula 12 includes an outer surface 18 and an inner surface 20. Inner surface 20 defines a passageway 22. Passageway 22 extends the entire length of cannula 12 and has a cylindrical cross sectional configuration having a uniform diameter along the length of passageway 22. In some embodiments, passageway 22 may have alternate cross section configurations, such as, for example, oval, oblong, triangular, square, hexagonal, polygonal, irregular, uniform, non-uniform and/or tapered.

A rod, such as, for example, a stylet 24 is configured for moveable disposal within passageway 22. Stylet 24 includes a distal end 26 ending with a blunt distal tip 28. The blunt distal tip 28 is specifically designed so as to be an atraumatic tip. That is, the blunt distal tip 28 is specifically designed so as to prevent or minimize damage to tissue as the device in used in situ. The distal blunt tip 28 can have different configurations such as circular, oval, arcuate, trapezoidal with rounded corners or any other configuration that would not damage tissue as the device is used in situ. The surface of the blunt distal tip 28 is non-abrasive so that it slides across tissue as the device is moved about at the surgical site and does not damage adjacent tissue. Distal end 26 is configured for disposal outside distal end 16 of cannula 12.

An expandable member, such as, for example, an expandable cage 30 is disposed with distal end 16 of cannula 12. Expandable cage 30 includes a proximal end 32 and a distal end 34. Proximal end 32 is disposed with distal end 16 of shaft 12. Distal end 34 is connected to distal end 26 of stylet 24 such that blunt distal tip 28 is exposed. Expandable cage 30 includes an outer surface 36 and an inner surface 38. Surface 36 defines a cavity 40 extending the entire length of cage 30. Cage 30 includes at least one wall 42 extending between surfaces 36 and 38 and defines a thickness t. Stylet 24 is configured to expand and collapse expandable cage 30. It is envisioned that the shapes and sizes of cage 30 when in the expanded configuration can be selected to provide a desired result during a procedure. For example, cage 30 may include shapes such as spheres, cylinders, etc. and have different dimensions to make cage 30 narrower or wider in a longitudinal direction, or extend further in a radial direction.

In one embodiment, the distal end 34 of the expandable cage 30 is attached to a ring-shaped member 48 having an inner surface defining an opening. The opening having a diameter that is smaller than the cross-section of the blunt tip 28 so that the blunt tip 28 is positioned within the opening but cannot pass through the opening. Stylet 24 is positioned within the opening of the ring shaped member 48 and attached to the distal blunt tip 28 so that when the stylet 24 is pulled towards cannula 12 the blunt tip 28 draws the ring shaped member 48 in the same direction so as to cause the cage 30 to expend. Similarly, when the stylet is moved away from distal end 16 of cannula 12 the cage 30 contracts to give a slimmer profile.

In one embodiment, the cage 30 comprises a plurality of walls 42 in the form of elongated strips that are spaced apart from one another and attached to the ring shaped member 48 at one end of the cannula 12 at the other end. In this embodiment, when the stylet 24 is drawn towards the cannula 12 the distance between each elongated strip increases so as to expand the cage 30 to an expanded configuration. Similarly, when the stylet 24 is moved away from the distal end 16 of cannula 12 the distance between the elongated strips returns back to the original position and cage 30 contracts to an unexpected configuration.

In one embodiment, at least one electrode 44 is disposed with cage 30. Electrode 44 is configured to emit an RF frequency for cutting and/or destroying tissue or nerves. In one embodiment, as shown in FIG. 1, electrode 44 is disposed on outer surface 36. In one embodiment, electrode 44 is disposed on inner surface 38. In one embodiment, electrode 44 is disposed within wall 42. Electrode placement can be varied depending on the required contact with the ligamentum flavum and the particular procedure. Electrode 44 can be of any shape such as, for example, straight, helical or curved. If more than one electrode 44 is provided, they can be positioned symmetrically or directionally along cage 30. The RF signal is configured to ablate a hypertrophied ligamentum flavum in lumbar spinal stenosis. The RF signal is configured to be maintained at a subablative controlled temperature.

In one embodiment, as shown in FIG. 2, a balloon 46 is disposed at distal end 16 of cannula 12 and within cavity 40. Balloon 46 is configured to distract an interlaminar space. Cannula 12 may be attached to a fill tube (not shown) such that a material, such as, for example, saline, a contrast solution or compressed air may be delivered from the tube, through passageway 22 and into balloon 46. As the material fills balloon 46, balloon 46 moves from an unexpanded configuration, to an expanded configuration such that balloon 46 also expands cage 30. It is envisioned that the shapes and sizes of balloon 46 when in the expanded configuration can be selected to provide a desired result during a procedure. For example, balloon 46 may include shapes such as spheres, cylinders, etc. and have different dimensions to make balloon 46 narrower or wider in a longitudinal direction, or extend further in a radial direction. Balloon 46 comprises a compliant material, such as, for example, polyurethane, polyethane, polyethylene, silicone, cronoprene or non-compliant material such as Nylon.

It is envisioned that balloon 46 can be a single or multi-layered balloon where each balloon layer has the same diameter and/or wall thickness, is comprised of the same material or materials having substantially identical mechanical properties, and has the same degree of molecular orientation in the body portion of the balloon. It will be apparent that in some situations it will be desirable to have some balloon layers having different thicknesses, materials, and/or degree of molecular orientations upon deflation, while at the same time having equivalent size, mechanical properties, and/or orientation upon inflation or expansion. For other applications, it will be apparent that one can vary size, material, and/or orientation to at least some degree, depending upon the requirements of a particular application.

It is contemplated that balloon 46 may include an impenetrable structural layer having low friction surfaces so as to facilitate deployment through a delivery tube, such as, for example, through cannula 12 and prevent rupture of balloon 46 as it is inflated or expanded in situ. Further variations are contemplated involving different combinations of lubricating layers and structural layers. In some embodiments, structural layers of balloon 46 can contain polyamides, polyesters, polyethylenes, polyurethanes, their co-polymers and combinations thereof.

In one embodiment, a cooling mechanism (not shown) is provided and is configured to cool balloon 46 and/or cage 30. In one embodiment, active cooling is providing by the cooling mechanism including a cooling tube connected to a liquid pumping system (not shown). In one embodiment, passive cooling is providing by having the cooling mechanism include cooling the inflation material prior to filling balloon 46.

In some embodiments, cannula 12 and/or balloon 46 and/or cage 30 includes one or a plurality of marker bands (not shown) comprising a radiopaque material. In one embodiment, the polymeric material is polyether block amide. In some embodiments, the highly radiopaque material incorporated into the polymeric material is barium sulfate, bismuth subcarbonate, tungsten, or a combination thereof.

In assembly, operation and use, system 10 is employed with a surgical procedure, such as, for a treatment of a hypertrophied ligamentum flavum. It is contemplated that one or all of the components of system 10 can be delivered or implanted as a pre-assembled device or can be assembled in situ. System 10 may be completely or partially revised, removed or replaced. It is envisioned that system 10 may also be used to treat other affected portions of the patient, such as, for example, a calcaneus bone, bones of the feet or hands, bones of the spine, bones of the arms and legs, etc.

In use, to a hypertrophied ligamentum flavum, the medical practitioner obtains access to a surgical site including in any appropriate manner, such as through the skin, or through an incision and retraction of tissues. In one embodiment, a drill is employed to remove bone tissue to provide access to a repair site. It is envisioned that system 10 can be used in any existing surgical method or technique including open surgery, mini-open surgery, minimally invasive surgery and percutaneous surgical implantation, whereby the fractured or injured bone is accessed through a mini-incision or sleeve that provides a protected passageway to the area. Once access to the surgical site is obtained, the particular surgical procedure can be performed for treating the injury or disorder. The configuration and dimension of system 10 is determined according to the configuration, dimension and location of a selected section of nerves and the requirements of a particular application.

An incision is made in the body of a patient and a cutting instrument (not shown) creates a surgical pathway for implantation of components of system 10. This may include the use of a cannula or other device. A preparation instrument (not shown) can be employed to prepare tissue surfaces, as well as for aspiration and irrigation of a surgical region according to the requirements of a particular surgical application.

Cage 30 is inserted to the surgical site and stylet 24 is manipulated to obtain the proper positioning of cage 30. Blunt distal tip 28 prevents adjacent tissue from being damaged. Once cage 30 is properly positioned, RF signals are emitted through electrodes 44. Stylet 24 can be manipulated to collapse cage 30 for removal from the patient.

In one embodiment, balloon 46 may be inserted through cannula 12 and is inflated with an inflation material to distract the interlaminar space. In one embodiment, inflation material can be delivered via a single gas source with a manifold and independently controlled valves such that the valves may be employed in controlled pressurized fluid flow to balloon 46. Other inflation methods are also contemplated.

A material, such as, for example, saline, a contrast solution or compressed air may be delivered through cannula 12 and passageway 22 and into balloon 46. The material may be delivered until balloon 46 assumes the desired profile. Balloon 46 can be manipulated to move bone and create a void at the desired location by viewing balloon 46 with use of markers. Removal of the material from balloon 46 to move from the expanded configuration to the unexpanded for removal form the patient.

In some embodiments, shaft 12 and/or balloon 46 and/or cage 30 includes one or a plurality of marker bands (not shown) comprising a radiopaque material. In one embodiment, the polymeric material is polyether block amide. In some embodiments, the highly radiopaque material incorporated into the polymeric material is barium sulfate, bismuth subcarbonate, tungsten, or a combination thereof.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto. The balloon can be modified or extended to accommodate particular formulations of balloon construction materials or fabrication techniques. Different balloon materials and surface coatings, or outer layers of different materials or surface coatings may also be applied to the balloon to facilitate a smaller balloon profile, biocompatibility, lubrication as well as other properties. The embodiments above can also be modified so that some features of one embodiment are used with the features of another embodiment. One skilled in the art may find variations of these preferred embodiments, which, nevertheless, fall within the spirit of the present invention, whose scope is defined by the claims set forth below.

What is claimed is:

1. A device for performing a surgical procedure comprising:
    an elongated shaft extending between a proximal end and a distal end and includes an outer surface and an inner surface, the inner surface defining a passageway;
    a stylet configured for moveable disposal within the passageway of the elongated shaft and the stylet includes a blunt distal tip configured for disposal outside the distal end of the elongated shaft and to prevent damage to adjacent tissue;
    an expandable member including a proximal end and a distal end comprising a ring-shaped member, wherein the expandable member comprises a plurality of elongated strips that are spaced apart from one another, the strips each comprising an inner surface having a proximal end that is fixed to the outer surface of the elongate shaft at the distal end of the elongated shaft and a distal end that engages an outer surface of the ring-shaped member, the ring-shaped member comprising an inner surface defining an opening, the blunt distal tip being positioned within the opening such that the blunt distal tip cannot pass through the opening to connect the expandable member to the stylet; and
    at least one electrode disposed with the expandable member.

2. A device as recited in claim 1, wherein the expandable member includes a wall defining a thickness and the at least one electrode is disposed within the thickness of the wall.

3. A device as recited in claim 1, wherein the expandable member includes an outer surface and the at least one electrode is disposed on the outer surface.

4. A device as recited in claim 1, wherein the expandable member includes an inner surface and the at least one electrode is disposed on the inner surface.

5. A device as recited in claim 1, further including a cooling mechanism in communication with a liquid pumping system and configured for disposal with the expandable member.

6. A device as recited in claim 1, wherein the at least one electrode is configured to emit a RF signal to ablate tissue.

7. A device as recited in claim 6, wherein the RF signal is configured to be maintained at a subablative controlled temperature.

8. A device as recited in claim 1, wherein the elongated shaft defines a longitudinal axis extending between the proximal and distal ends of the elongated shaft and the stylet is configured to move relative to the elongated shaft in a first direction along the longitudinal axis to expand the expandable member and to move relative to the elongated shaft in an opposite second direction along the longitudinal axis to collapse the expandable member.

9. A device as recited in claim 1, wherein the device includes a balloon disposed within the expandable member and configured to distract an interiaminar space.

10. A device for ablating tissue comprising:
    a cannula extending between a proximal end and a distal end and includes an outer surface and an inner surface, the inner surface defining a passageway;
    a stylet configured for moveable disposal within the passageway of the cannula and the stylet includes a blunt distal tip configured for disposal outside the distal end of the cannula and to prevent damage to adjacent tissue;
    an expandable cage including a proximal end and a distal end comprising a ring-shaped member, wherein the expandable cage comprises a plurality of elongated strips that are spaced apart from one another, the strips each comprising an inner surface having a proximal end that is fixed to the outer surface of the cannula at the distal end of the cannula and a distal end that engages an outer surface of the ring-shaped member, the ring-shaped member comprising an inner surface defining an opening, the blurt distal tip being positioned within the opening such that the blunt distal tip cannot pass through the opening to connect the expandable cage to the stylet; and
    at least one RF electrode disposed with the expandable cage.

11. A device as recited in claim 10 wherein the expandable cage includes a wall defining a thickness and the at least one RF electrode is disposed within the thickness of the wall.

12. A device as recited in claim 10, wherein the expandable cage includes an outer surface and the at least one RF electrode is disposed on the outer surface.

13. A device as recited in claim 10, wherein the expandable cage includes an inner surface and the at least one RF electrode is disposed on the inner surface.

14. A device as recited in claim 10, further including a cooling mechanism in communication with a liquid pumping system and configured for disposal with the expandable cage.

15. A device as recited, in claim 10, wherein a RF signal emitted by the at least one RF electrode is configured to be maintained at a subablative controlled temperature.

16. A device as recited in claim 10, wherein the stylet is configured to expand and collapse the expandable cage.

17. A device as recited in claim 10, wherein the device includes a balloon disposed within the expandable cage and configured to distract an interlaminar space.

18. A method for ablating tissue at a surgical site comprising:
providing a device comprising:
a cannula extending between a proximal end and a distal end and includes an outer surface and an inner surface, the inner surface defining a passageway;
a stylet configured for moveable disposal within the passageway of the cannula and the stylet includes a blunt distal tip configured for disposal outside the distal end of the cannula and to prevent damage to adjacent tissue;
an expandable cage including a proximal end and a distal end comprising a ring-shaped member, wherein the expandable cage comprises a plurality of elongated strips that are spaced apart from one another, the strips each comprising an inner surface having a proximal end that is fixed to the outer surface of the cannula at the distal end of the cannula and a distal end that engages an outer surface of the ring-shaped member, the ring-shaped member comprising an inner surface defining an opening, the blunt distal tip being positioned within the opening such that the blunt distal tip cannot pass through the opening to connect the expandable cage to the stylet; and
at least one RF electrode disposed with the expandable cage; creating an access path to the surgical site;
inserting the expandable cage into the surgical site and extending the stylet to expand the expandable cage; and
emitting RF signals through the at least one RF electrode to thermally ablate tissue.

19. A method as recited in claim 18, further including manipulating a balloon to move bone and create a void, wherein the balloon is disposed within the expandable cage and configured to distract an interlaminar space.

* * * * *

UNITED STATES PATENT AND TRADEMARK OFFICE
CERTIFICATE OF CORRECTION

| | | |
|---|---|---|
| PATENT NO. | : 9,028,488 B2 | Page 1 of 1 |
| APPLICATION NO. | : 13/803146 | |
| DATED | : May 12, 2015 | |
| INVENTOR(S) | : Goshayeshgar | |

It is certified that error appears in the above-identified patent and that said Letters Patent is hereby corrected as shown below:

On the Title Page, in item (71), under "Applicant", in Column 1, Line 1, insert -- Neuchatel -- and delete "Neuchâtel", therefor.

Specification

In Column 6, Line 7, delete "polyaetide" and insert -- polyketide --, therefor.

In Column 6, Line 8, delete "polycaroplaetohe" and insert -- polycaprolactone --, therefor.

In Column 7, Line 22, delete "end of" and insert -- end and --, therefor.

In Column 7, Line 26, delete "from the distal" and insert -- from distal --, therefor.

In Column 7, Line 29, delete "unexpected" and insert -- unexpanded --, therefor.

In Column 7, Line 62, delete "cronoprene" and insert -- chronoprene --, therefor.

In Column 9, Line 25, delete "form" and insert -- from --, therefor.

Claims

In Column 10, Line 38, in Claim 9, delete "interiaminar" and insert -- interlaminar --, therefor.

In Column 11, Line 7, in Claim 15, delete "recited, in" and insert -- recited in --, therefor.

Signed and Sealed this
First Day of March, 2016

Michelle K. Lee
*Director of the United States Patent and Trademark Office*